(12) United States Patent
Hoon

(10) Patent No.: US 9,556,491 B2
(45) Date of Patent: *Jan. 31, 2017

(54) UTILITY OF B-RAF DNA MUTATION IN DIAGNOSIS AND TREATMENT OF CANCER

(75) Inventor: Dave S. B. Hoon, Los Angeles, CA (US)

(73) Assignee: JOHN WAYNE CANCER INSTITUTE, Santa Monica, CA (US)

( * ) Notice: Subject to any disclaimer, the term of this patent is extended or adjusted under 35 U.S.C. 154(b) by 1399 days.

This patent is subject to a terminal disclaimer.

(21) Appl. No.: 12/037,798

(22) Filed: Feb. 26, 2008

(65) Prior Publication Data

US 2008/0268449 A1    Oct. 30, 2008

Related U.S. Application Data

(60) Provisional application No. 60/891,689, filed on Feb. 26, 2007, provisional application No. 60/893,243, filed on Mar. 6, 2007.

(51) Int. Cl.

| | |
|---|---|
| *A61K 6/00* | (2006.01) |
| *A61K 9/00* | (2006.01) |
| *A61K 9/48* | (2006.01) |
| *A61K 9/50* | (2006.01) |
| *A61K 9/51* | (2006.01) |
| *A61K 31/00* | (2006.01) |
| *A61K 31/70* | (2006.01) |
| *A61K 31/7088* | (2006.01) |
| *A61K 31/713* | (2006.01) |
| *A61K 47/00* | (2006.01) |
| *C12Q 1/68* | (2006.01) |

(52) U.S. Cl.
CPC ....... *C12Q 1/6886* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,004,750 A | 12/1999 | Frank-Kamenetskii et al. | |
| 7,442,507 B2 * | 10/2008 | Polsky et al. | 435/6.14 |
| 2004/0146879 A1 * | 7/2004 | Astle et al. | 435/6 |
| 2006/0246476 A1 | 11/2006 | Polsky et al. | |
| 2009/0053706 A1 * | 2/2009 | Laird et al. | 435/6 |

OTHER PUBLICATIONS

Turner et al. Detection of the BRAF V600E mutation in melanocytic lesions using the ligase detection reaction. J. Cutan. Pathol. 32: 334-339, 2005.*

Mouritzen, Peter et al. Single nucleotide polymorphism genotyping using locked nucleic acid (LNA). Expert. Rev. Mol. Diagn. 3(1): 27-38, 2003.*

PCT International Search Report, Aug. 18, 2008.

Taback at al., "Peptide Nucleic Acid Clamp PCR: A Novel K-ras Mutation Detection Assay for Colorectal Cancer Micrometastases in Lymph Nodes," Int. J. Cancer, vol. 111, pp. 409-414 (2004).

Kim et al., "Lymphatic Mapping Establishes the Role of BRAF Gene Mutation in Papillary Thyroid Carcinoma," Annals of Surgery, vol. 244, pp. 799-804 (2006).

Naoki et al., "Missense Mutations of the BRAF Gene in Human Lung Adenocarcinoma," Cancer Research 62, pp. 7001-7003 (2002).

Cohen et al., "BRAF Mutation in Papillary Thyroid Carcinoma," J. Nat'l. Cancer Institute, vol. 95, pp. 625-627 (2003).

Davies et al., "Mutations of the BRAF gene in human cancer," Nature, vol. 417, pp. 949-954 (2002).

Mercer et al., "Raf proteins and cancer: B-Raf is identified as a mutational target," Biochimica et Biophysica Acta 1653, pp. 25-40 (2003).

Wan et al., "Mechanism of Activation of the RAF-ERK Signaling Pathway by Oncogenic Mutations of B-RAF," Cell, vol. 116, pp. 855-867 (2004).

Weber et al., "Absence of Mutations of the BRAF Gene and Constitutive Activation of Extracellular-Regulated Kinase in Malignant Melanomas of the Uvea," The U.S. and Canadian Acad. of Pathology, Inc., vol. 83, pp. 1771-1776 (2003).

Shinozaki at al., "Incidence of BRAF Oncogene Mutation and Clinical Relevance for Primary Cutaneous Melanomas," Clinical Cancer Research, vol. 10, pp. 1753-1757 (2004).

Satyamoorthy et al., "Constitutive Mitogen-activated Protein Kinase Activation in Melanoma Is Mediated by Both BRAF Mutations and Autocrine Growth Factor Stimulation," Cancer Research 63, pp. 756-759 (2003).

Maldonado et al., "Determinants of BRAF Mutations in Primary Melanomas," J. Nat'l. Cancer Institute, vol. 95, pp. 1878-1880 (2003).

Dong et al., "BRAF Oncogenic Mutations Correlate with Progression rather than Initiation of Human Melanoma," Cancer Research 63, pp. 3883-3885 (2003).

Chang et al., "Clinical significance of BRAF mutations in metastatic melanoma," J. of Translational Med. 2004, pp. 1-5 (2004).

Omholt et al., NRAS and BRAF Mutations Arise Early during Melanoma Pathogenesis and Are Preserved throughout Tumor Progression, Clinical Cancer Research, vol. 9, pp. 6483-6488 (2003).

Akslen at al., "BRAF and NRAS Mutations Are Frequent in Nodular Melanoma but Are not Associated with Tumor Cell Proliferation or Patient Survival," J. Invest. Dermatol., vol. 125, pp. 312-317 (2005).

(Continued)

*Primary Examiner* — Alana Harris Dent
(74) *Attorney, Agent, or Firm* — Perkins Coie LLP; Lara J. Dueppen

(57) ABSTRACT

The present invention discloses a method of detecting a wild-type or mutant B-RAF gene in a body fluid sample from a subject. Also disclosed are methods of using B-RAF as a biomarker for detecting cancer, predicting the outcome of cancer, and monitoring the treatment of cancer or the status of cancer. Furthermore, the invention discloses methods and compositions for detecting a mutant gene with a peptide nucleic acid clamp capable of hybridizing to a wild-type gene and a locked nucleic acid probe capable of hybridizing to a mutant of the gene.

18 Claims, 3 Drawing Sheets

(56) References Cited

OTHER PUBLICATIONS

Kim, J. et al., Lymphatic mapping establishes the role of BRAF gene mutation in papillary thyroid carcinoma, Annals of Surgery, v. 244, No. 5, (Nov. 2006), pp. 799-804.

Nagai Y., et al., "Genetic heterogeneity of the epidermal growth factor receptor in non-small cell lung cancer cell lines by a rapid and sensitive detection system, the peptide nucleic acid-locked nucleic acid PCR clamp," Cancer Research, v. 65, No. 16, (Aug. 15, 2005), pp. 7276-7282.

Tanaka T., et al., "Reliability of the peptide nucleic acid-locked nucleic acid polymerase chain reaction clamp-based test for epidermal growth factor receptor mutations integrated into the clinical practice for non-small cell lung cancers," Cancer Science, v. 98, No. 2, (Feb. 2007), pp. 246-252.

Luo, Ji-Dung et al., "Detection of rate mutant K-ras DNA in a single-tube reaction using peptide nucleic acid as both PCR clamp and sensor probe," Nucleic Acids Research, Oxford Univ. Press, GB LNKD—DOI:10.1093/NAR/GNJ008, v. 34, No. 2, (Jan. 1, 2006), E12, pp. 1-7.

Behn, M. et al., "Sensitive detection of p53 gene mutations by a 'mutant enriched' pCR-SSCP technique," Nucleic Acids Research, Oxford Univ. Press, Surrey, GB, v. 26, No. 5, (Mar. 1, 1998), pp. 1356-1358.

O'Day, S.J. et al., "Maintenance biotherapy for metastatic melanoma with interleukin-2 and granulocyte macrophage-colony stimulating factor improves survival for patients responding to induction concurrent biochemotherapy," Clinical Cancer Research, v. 8, (Sep. 2002), pp. 2775-2781.

Shinozaki, M. et al., "Utility of circulating B-RAF mutation in serum for monitoring melanoma patients receiving biochemotherapy," Clinical Cancer Research, v. 13, No. 7, (Apr. 1, 2007), pp. 2068-2074.

European Search Report dated Jun. 29, 2010 in the corresponding European Patent Application No. EP 08740764, pp. 1-4.

Henry Ford Health System, BRAF V600E mutation detection, 2 pgs (2012).

Kumar et al., BRAF mutations in metastatic melanoma: a possible association with clinical outcome, Clin Cancer Res vol. 9, 3362-3368 (2003).

European Patent Office, Exam Report for EP08730764.1, Mar. 13, 2013.

IP Australia, Patent Examination Report No. 1 for AU2008221468, Oct. 15, 2012.

IP Australia, Patent Examination Report No. 2 for AU2008221468, Jul. 14, 2014.

IP Australia, Patent Examination Report No. 1 for AU2014204427, Feb. 18, 2016.

* cited by examiner

UTILITY OF B-RAF DNA MUTATION IN DIAGNOSIS AND TREATMENT OF CANCER

RELATED APPLICATIONS

The present application claims priority to U.S. provisional Application Ser. No. 60/891,689 filed on Feb. 26, 2007 and 60/893,243 filed on Mar. 6, 2007, the contents of both of which are incorporated herein by reference in their entity.

FUNDING

This invention was made with support in part by grants from NIH (POCA029605, POCA012582, and R33-CA100314). Therefore, the U.S. government has certain rights.

FIELD OF THE INVENTION

The present invention relates in general to management of cancer. More specifically, the invention provides methods of using the B-RAF gene (wild-type and mutant) as a biomarker in assessment of cancer patients for detection, prognosis, and monitoring therapy.

BACKGROUND OF THE INVENTION

The management of cutaneous melanoma continues to pose a significant challenge. Clinical prognostic factors have not been shown to predict disease recurrence and overall survival in patients with metastatic disease. Adjuvant therapy for melanoma can have major side effects, and can be associated with significant morbidity. In addition, it has been difficult to identify which patients will respond to the few treatment options available, as well to predict disease recurrence and progression.

Over the last decade, advances in melanoma translational research have attempted to identify key components in molecular and genetic alterations that affect the progression of this disease (1). High-throughput genomic approaches have been focused on identifying gene aberrations in the RAS-RAF-MEK-ERK-MAP kinase signaling pathway, since they have been shown to regulate cellular differentiation, proliferation, and apoptosis (2-4).

SUMMARY OF THE INVENTION

The invention is based, at least in part, upon the unexpected discovery that circulating B-RAF mutation (B-RAF-mut) can be used for diagnosis of cancer bearing B-RAF mutation and monitoring cancer patient response to treatment. Accordingly, the invention provides an assay for detecting circulating B-RAF mutation (V600E) or wild type DNA in cancer patients and its clinical utility.

More specifically, in one aspect, the invention features a method of detecting a wild-type or mutant B-RAF gene in a subject. The method comprises obtaining from a subject a body fluid sample containing DNA and detecting a wild-type or mutant B-RAF gene in the sample.

In another aspect, the invention features a method of detecting cancer in a subject. The method comprises obtaining from a subject a body fluid sample containing DNA and detecting a mutant B-RAF gene in the sample. The presence of the mutant B-RAF gene indicates that the subject is suffering from cancer.

In yet another aspect, the invention features a method of predicting the outcome of cancer. The method comprises obtaining a tissue or body fluid sample containing DNA from a test subject suffering from cancer and detecting a mutant B-RAF gene in the sample. The presence of the mutant B-RAF gene indicates that the test subject has a lower probability to survive or be a responder to a cancer therapy than a control subject who suffers from cancer but does not have the mutant B-RAF gene. In some embodiments, the sample is obtained from the test subject prior to the cancer therapy; in other embodiments, the sample is obtained from the test subject following the cancer therapy.

In still another aspect, the invention features a method of monitoring the treatment of cancer. The method comprises treating a subject suffering from cancer with a cancer therapy, obtaining a tissue or body fluid sample containing DNA from the subject, and detecting a mutant B-RAF gene in the sample. The amount of the mutant B-RAF gene after the treatment, if less than the amount of the mutant B-RAF gene before the treatment, indicates that the subject is likely to be a responder to the therapy.

The invention further provides a method of monitoring the status of cancer in a subject. The method comprises obtaining a first body fluid sample containing DNA from a subject suffering from cancer at a first time point, obtaining a second body fluid sample containing DNA from the subject at a second time point subsequent to the first time point, and detecting the amount of a mutant B-RAF gene in the first and second sample. If the amount of the mutant B-RAF gene in the second sample is more than the amount of the mutant B-RAF gene in the first sample, the cancer is likely to have progressed in the subject. On the other hand, if the amount of the mutant B-RAF gene in the second sample is less than the amount of the mutant B-RAF gene in the first sample, the cancer is likely to have regressed in the subject.

The invention also provides a method of detecting a mutant B-RAF gene. The method comprises providing a sample (e.g., a tissue or body fluid sample obtained from a subject) containing DNA and a peptide nucleic acid clamp capable of hybridizing to a wild-type B-RAF gene and detecting a mutant B-RAF gene in the sample. In some embodiments, the mutant B-RAF gene is detected with a locked nucleic acid probe capable of hybridizing to the mutant B-RAF gene. In some embodiments, the mutant B-RAF gene is detected by a polymerase chain reaction.

In addition, the invention provides a method of detecting a mutant gene. The method comprises providing a sample (e.g., a tissue or body fluid sample obtained from a subject) containing DNA and a peptide nucleic acid clamp capable of hybridizing to a wild-type gene (e.g., a K-Ras, N-RAS, p53, receptor tyrosine kinases, EGFR, or RET gene) and detecting a mutant of the gene in the sample with a locked nucleic acid probe capable of hybridizing to the mutant gene. In some embodiments, the mutant gene is detected by a polymerase chain reaction.

In a method of the invention, the body fluid sample may be a blood, plasma, serum, or cerebral spinal fluid sample; the tissue sample may be a paraffin-embedded tissue sample; the cancer may be melanoma, thyroid cancer, colorectal cancer, lung cancer, or neurocancer; the mutant B-RAF gene may contain a B-RAF V600E mutation; and the cancer therapy may be a biochemotherapy.

Also with the invention is a composition comprising a peptide nucleic acid clamp capable of hybridizing to a wild-type gene (e.g., a B-RAF, K-Ras, N-RAS, p53, receptor tyrosine kinases, EGFR, or RET gene) and a locked nucleic acid probe capable of hybridizing to a mutant of the gene.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Figure 1:
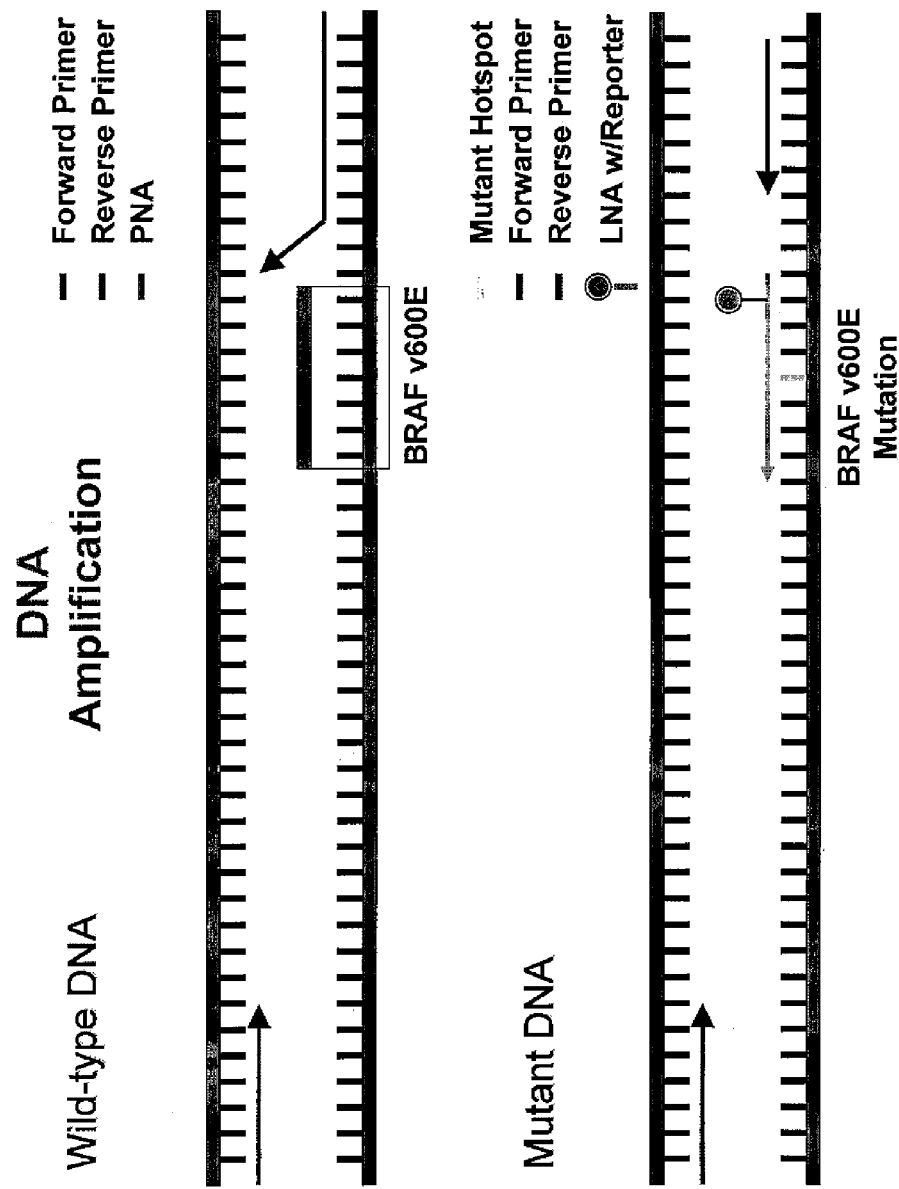
FIG. 1 is a schematic representation of PNA/LNA clamp directed PCR. Upper figure denotes PNA/wt DNA complex, with no amplification. Lower figure demonstrates amplification of DNA template containing B-RAFmt using the dual labeled LNA probe that recognizes and hybridizes to V600E.

The invention provides, among other things, a sensitive assay for the detection of B-RAFmut in blood, i.e., serum or plasma, and paraffin-embedded tissue. The detection of circulating B-RAFmut in blood allows one not to have tumor biopsy or specimen to assess for B-RAFmut, which can be used as a surrogate for monitoring patient before, during, and after treatment. The detection of circulating B-RAFmut can also be used to assess tumor destruction and for early detection of cancer, recurrence of cancer, and progression of cancer. The major applicable cancers that have significant B-RAF mutation include, but are not limited to, melanoma, thyroid cancer, colorectal cancer, lung cancer, and neurocancer.

Accordingly, one method of invention involves obtaining from a subject a body fluid sample containing DNA and detecting a wild-type or mutant B-RAF gene in the sample.

As used herein, a "subject" refers to a human or animal, including all mammals such as primates (particularly higher primates), sheep, dog, rodents (e.g., mouse or rat), guinea pig, goat, pig, cat, rabbit, and cow. In a preferred embodiment, the subject is a human. In another embodiment, the subject is an experimental animal or animal suitable as a disease model.

The term "body fluid" refers to any body fluid in which cellular or acellular DNA may be present, including, without limitation, blood, serum, plasma, bone marrow, cerebral spinal fluid, peritoneal/pleural fluid, lymph fluid, ascite, serous fluid, sputum, lacrimal fluid, stool, and urine. "Cellular DNA" refers to DNA that exists within a cell or the isolated form of such DNA; "acellular DNA" refers to DNA that exists outside a cell in a subject or the isolated form of such DNA.

Body fluid samples can be obtained from a subject using any of the methods known in the art. Methods for extracting cellular DNA from body fluid samples are well known in the art. Typically, cells are lysed with detergents. After cell lysis, proteins are removed from DNA using various proteases. DNA is then extracted with phenol, precipitated in alcohol, and dissolved in an aqueous solution. Methods for extracting acellular DNA from body fluid samples are also known in the art. Commonly, acellular DNA in a body fluid sample is separated from cells, precipitated in alcohol, and dissolved in an aqueous solution.

A "wild-type" gene is the typical form of a gene as it occurs in nature; a "mutant" gene arises or results from an instance of mutation, which is a structural change within the DNA of a gene resulting in the creation of a new gene different from the wild-type gene.

The B-RAF gene encodes a serine threonine kinase downstream for RAS in the MAP kinase pathway that transduces regulatory signals from RAS through MAPK (8-11). Mutations in the B-RAF gene are known to be present at multiple sites (5-8), and clustering around exons 11 and 15 of the gene in the kinase domain is quite frequent (5, 6, 12). For example, the V600E (formerly V599E) amino acid missense mutation resulting from a 1796T→A transversion in exon 15 is the predominant mutation in melanoma (13).

Wild-type and mutant B-RAF genes can be detected and quantified using any of the methods described in the instant application or those well known in the art. For instance, as described in detail below, a mutant B-RAF gene containing a B-RAF V600E mutation may be detected and quantified by real-time quantitative RT-PCR using a peptide nucleic acid clamp capable of hybridizing to the wild-type B-RAF gene and a locked nucleic acid probe capable of hybridizing to the mutant B-RAF gene. Alternatively, wild-type and mutant B-RAF genes may be detected and quantified by sequencing.

Another method of the invention relates to detecting cancer in a subject. A body fluid sample containing DNA is obtained from a subject and a mutant B-RAF gene in the sample is detected as described above. If the mutant B-RAF gene is present in the sample, the subject is suffering from cancer.

As used herein, "cancer" refers to a disease or disorder characterized by uncontrolled division of cells and the ability of these cells to spread, either by direct growth into adjacent tissue through invasion, or by implantation into distant sites by metastasis. Exemplary cancers include, but are not limited to, primary cancer, metastatic cancer, AJCC stage I, II, III, or IV cancer, carcinoma, lymphoma, leukemia, sarcoma, mesothelioma, glioma, germinoma, choriocarcinoma, prostate cancer, lung cancer, breast cancer, colorectal cancer, gastrointestinal cancer, bladder cancer, pancreatic cancer, endometrial cancer, ovarian cancer, melanoma, brain cancer, testicular cancer, kidney cancer, skin cancer, thyroid cancer, head and neck cancer, liver cancer, esophageal cancer, gastric cancer, intestinal cancer, colon cancer, rectal cancer, myeloma, neuroblastoma, and retinoblastoma. Preferably, the cancer is melanoma, thyroid cancer, colorectal cancer, lung cancer, or neurocancer.

The invention further provides a method of predicting the outcome of cancer by obtaining a tissue or body fluid sample containing DNA from a test subject suffering from cancer and detecting a mutant B-RAF gene in the sample. The sample may be obtained from the test subject either prior to or following the therapy. If the mutant B-RAF gene is present in the sample, the test subject has a lower probability to survive or be a responder to a cancer therapy compared to a control subject who suffers from cancer but does not have the mutant B-RAF gene.

A "tissue" sample from a subject may be a biopsy specimen sample, a normal or benign tissue sample, a cancer or tumor tissue sample, a freshly prepared tissue sample, a frozen tissue sample, a paraffin-embedded tissue sample, a primary cancer or tumor sample, or a metastasis sample. Exemplary tissues include, but are not limited to, epithelial, connective, muscle, nervous, heart, lung, brain, eye, stomach, spleen, bone, pancreatic, kidney, gastrointestinal, skin, uterus, thymus, lymph node, colon, breast, prostate, ovarian, esophageal, head, neck, rectal, testis, throat, thyroid, intestinal, melanocytic, colorectal, liver, gastric, and bladder tissues.

Methods for obtaining tissue samples from a subject are well known in the art. Cellular and acellular DNA may be extracted from these samples using any of the methods known in the art, for example, methods similar to those described above.

A "cancer therapy" refers to administration of a substance to a subject suffering from cancer or a surgical operation in a subject suffering from cancer with the purpose to cure, alleviate, relieve, remedy, prevent, or ameliorate cancer, symptoms of cancer, a disease state secondary to cancer, or predisposition toward cancer.

For example, chemotherapy is commonly used to treat cancer. It involves use of chemical agents to stop cancer cells from growing. When surgery is used for treatment of cancer, the cancer and some tissue adjacent to the cancer are typically removed. Additional cancer treatments involve radiation therapy, biological therapy (i.e., immunologic therapy, immunotherapy, biotherapy), and hormonal therapy. Biological therapy uses the body's immune system to help kill cancer cells. Types of biological therapy include interferon, interleukin, monoclonal antibodies, colony-stimulating factors, cytokines, and vaccines. Hormones are naturally occurring substances in the body that stimulate the growth of hormone-sensitive tissues, such as the breast or the prostate gland. When cancer forms in breast or prostate tissue, its growth and spread may be caused by the body's own hormones. Therefore, hormonal therapy involves drugs that block hormone production or change the way hormones work, and the removal of organs that secrete hormones, such as the ovaries or testicles. Biochemotherapy is the use of immunotherapy in conjunction with chemotherapy.

"Responders" to a cancer therapy are subjects whose tumors decrease in size after the treatment. The response to the treatment may be a partial response (PR) or a complete response (CR). "Non-responders" to a cancer therapy are subjects who develop progressive disease (PD) after the treatment.

Moreover, the invention provides a method of monitoring the treatment of cancer. A subject suffering from cancer is treated with a cancer therapy. A tissue or body fluid sample containing DNA is obtained from the subject. A mutant B-RAF gene in the sample is then detected and quantified. If the amount of the mutant B-RAF gene after the treatment is less than the amount of the mutant B-RAF gene before the treatment, the subject is likely to be a responder to the therapy.

The present invention additionally provides a method of monitoring the status of cancer in a subject. A first body fluid sample containing DNA is obtained at a first time point from a subject suffering from cancer. A second body fluid sample containing DNA is obtained from the subject at a second time point subsequent to the first time point. The amount of a mutant B-RAF gene is then detected in the first and second sample. If the amount of the mutant B-RAF gene in the second sample is more than the amount of the mutant B-RAF gene in the first sample, the cancer is likely to have progressed in the subject; if the amount of the mutant B-RAF gene in the second sample is less than the amount of the mutant B-RAF gene in the first sample, the cancer is likely to have regressed in the subject.

Another object of the invention is to provide a method of detecting a mutant B-RAF gene by providing a sample containing DNA and a peptide nucleic acid clamp capable of hybridizing to a wild-type B-RAF gene and detecting a mutant B-RAF gene in the sample.

A sample of the invention may be a tissue or body fluid sample obtained from a subject as described above.

Peptide nucleic acids (PNAs) are high-affinity DNA synthetic analogs that hybridize with complementary DNA (20). PNAs have N-(2-aminoethyl)-glycine units as backbones. PNA-DNA hybrids are more stable than those for cDNA-DNA, and are highly sensitive and specific in distinguishing single base pair mismatches. In addition, as PNA oligomers cannot function as primers in PCR reactions, they can be used as blockers to prevent amplification of wild-type DNA templates (21). PNA clamps are known to those skilled in the art. See, e.g., U.S. Pat. No. 6,004,750.

In some embodiments, the mutant B-RAF gene is detected with a locked nucleic acid (LNA) probe capable of hybridizing to the mutant B-RAF gene. LNA, often referred to as inaccessible RNA, is a modified RNA nucleotide. The ribose moiety of a LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in an oligonucleotide whenever desired. Such oligomers are commercially available. The locked ribose conformation enhances base stacking and backbone pre-organization. This significantly increases the thermal stability (melting temperature) of oligonucleotides. See, e.g., Kaur et al. (2006) Thermodynamic, Counterion, and Hydration Effects for the Incorporation of Locked Nucleic Acid Nucleotides into DNA Duplexes. Biochemistry 45 (23):7347-55. LNAs also have higher affinity to DNA than cDNA, and are highly sensitive and specific in distinguishing single base pair mismatches.

A PNA clamp and LNA probe technique based quantitative real-time PCR assay can be used to detect a mutant gene in a sample. It is particularly useful in detecting single base pair mutations in a sample that requires a high sensitivity because the amount of the target DNA is low in the sample.

A method of the invention for detecting a mutant gene involves providing a sample containing DNA and a PNA clamp capable of hybridizing to a wild-type gene and detecting a mutant of the gene in the sample with a LNA probe capable of hybridizing to the mutant gene. This method may be used to detect a mutant gene such as a mutant B-RAF, K-Ras, N-RAS, p53, receptor tyrosine kinases, EGFR, or RET gene.

Also within the invention is a composition comprising a PNA clamp capable of hybridizing to a wild-type gene and a LNA probe capable of hybridizing to a mutant of the gene. The composition may be used to detecting the mutant gene in a sample. The composition may be packaged into a kit, which may further contain reagents for PCR reactions.

The following example is intended to illustrate, but not to limit, the scope of the invention. While such example is typical of those that might be used, other procedures known to those skilled in the art may alternatively be utilized. Indeed, those of ordinary skill in the art can readily envision and produce further embodiments, based on the teachings herein, without undue experimentation.

EXAMPLE

Abstract

Purpose.

Somatic B-RAF gene mutation has been identified in many malignancies and detected at a high frequency in cutaneous malignant melanoma. However, the significance of the B-RAF mutations (B-RAFmt) in terms of its prognostic and predictive capabilities for treatment response or disease outcome is not known. We hypothesized that circulating serum B-RAFmt (B-RAFsmt) at V600E detected in serum predicts response in melanoma patients receiving concurrent biochemotherapy (BC).

Experimental Design.

A real-time clamp quantitative RT-PCR (qRT) assay was designed to assess B-RAFsmt by PNA clamping and LNA hybrid probe. Normal (n=18) and AJCC stage I-IV melanoma patients (n=103) were evaluated. These included stage 1V patients (n=48) with blood drawn before and after BC. Patients were classified as BC responders or non-responders. Responders (n=24) had a complete or partial response following BC; non-responders (n=24) developed progressive disease.

Results.

Of the 103 melanoma patients, 38 (37%) had B-RAFsmt DNA, of which 11 of 34 (32%) were stage I/II and 27 of 69 (39%) were stage III/IV. Of the 48 BC patients, 10 of 24 (42%) patients were positive for the B-RAFsmt in the respective responder and non-responder groups before treatment. After BC, B-RAFsmt was detected in only 1 of 10 patients (10%) in the responder group and 7 of 10 patients (70%) in the non-responder group. B-RAFsmt is associated with significantly worse (p=0.039) overall survival in patients receiving BC.

Conclusion.

These studies demonstrate the presence and utility of circulating B-RAFsmt DNA in melanoma patients.

Introduction

B-RAF mutations (B-RAFmt) have been reported at a high frequency in melanoma, thyroid cancer, and lung cancer (5-8). B-RAF encodes a serine threonine kinase downstream for RAS in the MAP kinase pathway that transduces regulatory signals from RAS through MAPK (8-11). B-RAFmt have been found at multiple sites, whereby clustering around exon 11 and 15 of the gene in the kinase domain is quite frequent (5, 6, 12). In our recent study evaluating the frequency of B-RAFmt in melanoma progression, we found that the V600E (formerly V599E) amino acid missense mutation resulting from a 1796T→A transversion in exon 15 of B-RAF was the predominant mutation in the tumors assessed, and the mutation was found in 31% of primary melanoma and 57% of metastatic melanoma tumors (13). Since this mutation has been shown to significantly increase kinase activity and occurs at a significantly higher frequency than other gene mutations found in melanoma, such as N-RAS, $p16^{INK4a}$, and p53 (5, 14, 15), we hypothesized that the presence of circulating DNA with B-RAFmt at V600E in the serum of melanoma patients may be clinically relevant. We have previously shown that circulating DNA in the serum of melanoma patients has clinical utility as a marker for disease progression, identification of occult recurrences, and predicting response to surgical and adjuvant therapy (16-18). Mori et al. demonstrated a correlation between circulating methylated DNA in serum and disease progression, and showed an association between circulating methylated DNA and response to biochemotherapy (BC) (16, 19).

In this study, we developed a peptide nucleic acid (PNA) clamp and locked nucleic acid (LNA) probe technique based quantitative real-time PCR assay to detect serum circulating B-RAFsmt DNA of melanoma patients. The detection of single base pair mutations in circulating DNA requires a very sensitive assay, since the frequency of circulating B-RAFsmt DNA will be low. PNAs and LNAs are high-affinity DNA synthetic analogs that hybridize with complementary DNA (20). PNAs have N-(2-aminoethyl)-glycine units as backbones. PNA-DNA hybrids are more stable than those for cDNA-DNA, and are highly sensitive and specific in distinguishing single base pair mismatches. In addition, as PNA oligomers cannot function as primers in PCR reactions, they are used as blockers to prevent amplification of wild-type DNA templates (21). LNAs also have higher affinity to DNA than cDNA, and were incorporated into our assay for their specificity in recognizing single base-pair mismatches. LNA-DNA chimeras can be constructed for use as primers or probes. Highly specific detection of B-RAFsmt was achieved using a specific PNA clamping and LNA hybridizing probe.

The purpose of this study was to determine whether we could identify B-RAF V600E mutation on exon 15 as circulating DNA in the serum of melanoma patients, and to determine whether quantitative detection of the B-RAFmt could have potential clinical applicability in evaluating non-invasive disease progression or quantitative evaluation of therapeutic maneuvers. To date, detection of B-RAFmt (V600E) in melanoma tissue has not shown any significant correlation to disease outcome, although B-RAFmt in metastatic melanoma can be frequently detected in >55% of patients. In this study, we detected amounts of circulating mutant DNA with high sensitivity and specificity. To further investigate the possible clinical implications of the presence of the B-RAFsmt DNA, we collected sera from patients before and after treatment with BC. We hypothesized that the presence of B-RAFsmt in post-treatment serum may indicate absence of response to treatment.

Materials and Methods

Patients and Cell Line.

Fifty-five patients with different AJCC stages of melanoma were assessed for B-RAFsmt. In addition, fifty melanoma stage IV patients who received BC were also included for the treatment response study. Blood was drawn within one week prior to the start of BC and within four weeks after the last cycle. Median completed cycles of BC were six for the responder group and three for the non-responder group. Maximum number of cycles received were 6 cycles, as previously described (22, 23). These patients were further divided into two groups based on their response to BC (responders and non-responders). Patients whose tumors decreased in size after treatment (PR, partial response; CR, complete response) are grouped as responders (n=24), while those that had progressive disease (PD, progressive disease) are grouped as non-responders (n=24). Two patients had stable disease (SD, stable disease) and were removed from the final statistical analysis. The BC regimen was administered in 5-day periods at 21-day intervals, and included the administration of multi-agent chemotherapy, consisting of dacarbazine, cisplatin, vinblastine, and tamoxifen, with the addition of the biologic response modifiers IL-2, and interferon α-2b. Patients were accrued through both the John Wayne Cancer Institute (JWCI) and The Angeles Clinic and Research Institute. Human Subjects Institutional Review Board (IRB) approval was obtained for the purposes of this study at the participating institutions. Signed informed consent was obtained from all patients. Serum samples from 18 healthy donors, which served as controls, were also analyzed.

Fourteen melanoma cell lines established and characterized at the JWCI, as previously described, were assessed for B-RAFmt (V600E) (24-26). The cell lines were grown in 10% heat-inactivated fetal calf serum (Gemini, Calabasas, Calif.) RPMI 1640 plus penicillin and streptomycin, as previously described, and assessed at early passages (24). DNA was extracted from cells when cultures reached 70-80% confluency.

DNA Extraction.

Blood was collected from patients in sodium citrate-containing tubes (Becton Dickinson, Franklin Lanes, N.J.). Plasma was immediately separated from blood cells by differential centrifugation at 1000×g for 15 min, filtered through a 13-mm serum filter (Fisher Scientific, Pittsburgh Pa.), and cryopreserved at −80° C. DNA was isolated from the serum using Qiagen mini-columns (Qiagen, Valencia, Calif.) according to the manufacturer's instructions, with modifications. Serum was precipitated with 1 µL of Pellet Paint® NF co-precipitant (Novagen, Madison, Wis.) before centrifuging proteinase-digested samples. DNA from cell lines was extracted using DNAzol® (Molecular Research Center, Cincinnati, Ohio) as previously described (27). All serum specimens were demonstrated to have DNA.

Oligo Design.

Briefly, primers were designed to amplify exon 15 of the B-RAF gene, including the mutation hot spot (V600E). PNA (Applied Biosystems, Foster City, Calif.) was designed to clamp the hot spot on the wild-type (wt) template and block the wild-type template from being amplified by PCR. A fluorescence resonance energy transfer (FRET) dual labeled LNA probe was designed and synthesized (Proligo, Boulder, Colo.) to recognize and hybridize at V600E, specifically the T to A mutation, as this mutation is the most frequently seen mutation for B-RAF at this hot spot (5). A second FRET DNA probe was purchased from Biosource (Camarillo, Calif.), and synthesized using the adjacent sequences to the LNA probe, avoiding the hot spot, in order to amplify and estimate the total number of DNA templates, both wild-type (wt) (V600E) and mutant (mt) (V600E), in the PCR reaction. Real-time quantitative PCR (qPCR) for mutation using both the PNA clamp and FRET LNA probe was performed in a separate reaction from the qPCR for total number of templates using the FRET DNA probe.

Real-Time Quantitative PCR and Quantification of B-RAFmt.

PCR was performed using the following primers and probe. B-RAF: 5'-CCTCACAGTAAAAATAGGTG-3' (forward); 5'-ATAGCCTCAATTCTTACCA-3, (reverse); 5'-CTACAGAGAAATCTCGAT-BHQ-1-3' (LNA); 5'-ATC-GAGATTTCACTGTAG-3' (PNA). The PCR assay was performed with the iCycler iQ real-time PCR Detection System (Bio-Rad Laboratories, Hercules, Calif.) (FIG. 1). Genomic DNA (20 ng) from paraffin-embedded tumors was amplified using real-time PCR (iCycler) in a 20 µL reaction containing each PCR primer, LNA, PNA, deoxynucleotide triphosphate, $MgCl_2$, PCR buffer, and AmpliTaq Gold Polymerase (Applied Biosystems, Branchburg, N.J.). Each PCR reaction was subjected to 55 cycles at 94° C. for 60 seconds, 72° C. for 50 seconds, 53° C. for 50 seconds, and 72° C. for 60 seconds. Each sample was assayed in triplicate with appropriate positive and negative cell line and reagent controls.

We established the MA cell line DNA as the standard for measuring units of V600E B-RAFmt target DNA (heterozygous); the amount of target mutant DNA contained in 1 µg/mL of MA genomic DNA was arbitrarily established to be 1 U of B-RAFmt. qPCR results of the samples, generated by iCycler, were compared to this standard to quantify the relative units of B-RAFmt in all the samples. All PCR assays for mutant sequence analysis were performed in triplicate, and the median was used for data analysis.

Representative B-RAFmt V600E and B-RAFwt V600E tumors (n=4) were sequenced to confirm the accuracy of the PCR assay, as previously described (5). PCR amplification was performed using the following primers for B-RAF: 5'-TGTTTTCCTTTACTTACTACACCTCA-3' (forward); and 5'-AGCATCTCAGGGCCAAAAAT-3' (reverse). The PCR products were purified with QIAquick PCR Purification kit (Qiagen) and subsequently direct-sequenced at 58° C. using Dye Terminator Cycle Sequence Quick Start kit (Beckman Coulter, Fullerton, Calif.) according to the manufacturer's instructions. Dye-terminated products were assessed by capillary array electrophoresis on a CEQ8000XL Genetic Analysis System (Beckman Coulter).

BC Response: Evaluation of B-RAFsmt.

For data analysis, we used the ratio of B-RAFsmt DNA copies (in units equivalent to V600E mutation copies in µg/mL of MA DNA) to total B-RAFwt DNA templates (in units equivalent to V600E wt copies in 1 µg/mL of DNA) in the reaction as reported results. Mutant DNA copies were calculated by qPCR using a V600E mutant-specific FRET LNA probe with dilution series of MA DNA for the standard curve; total B-RAFwt DNA template copies were measured by qPCR with the FRET DNA probe to the V600E region. If the ratio for the post-BC serum decreased by one tenth or more when compared to the pre-BC serum sample, we determined that the patient 'decreased' in B-RAFsmt; if the ratio increased by ten fold or more, it was designated as 'increased'.

Biostatistical Analysis.

All clinicopathologic factors and B-RAFsmt frequency were compared by Student's t-test and Fisher's Exact test. Kaplan-Meier survival curve analysis was used to assess overall and disease-free survival. Univariate analysis of prognostic factors, including age, gender, ECOG status, the number of metastatic sites, the site of metastases (soft tissue, lymph nodes, and lung vs. other organs), lactate dehydrogenase (LDH) levels, and prior previous treatment (vaccine, chemotherapy, and/or interferon vs. no treatment) was assessed. A multivariate analysis using the Cox proportional hazard regression model was also performed to evaluate the prognostic significance of B-RAFsmt when clinical prognostic factors were adjusted. All analyses were performed using SAS (SAS/STAT User's Guide, version 8; SAS Institute Inc., Gary, N.C.) and tests were 2-sided with a significance level of <0.05.

Results

B-RAFmt Assay Sensitivity.

Using the melanoma cell line MA, shown to have B-RAFmt V600E, we performed several serial dilution studies to determine the sensitivity of the PNA clamp with the LNA hybridizing probe assay using real-time qPCR. MA DNA in µg/mL was diluted in lymphocyte DNA from normal individuals to simulate an in vivo model. The B-RAFmt could be detected in $1 \times 10^{-4}$ unit of MA DNA diluted in 10 U of lymphocyte DNA. However, no B-RAFmt (V600E) was detected when $1 \times 10^{-5}$ U of MA DNA was diluted in 10 U of lymphocyte DNA. In this series of dilutions, we observed that, at greater than 10 U of DNA as a template, the assay will detect amplification of the B-RAF wild-type (B-RAFwt, V600E) gene, as there is only a limited quantity of PNA in each reaction to block amplification of wild-type DNA. In keeping with this observation, we assessed each sample to estimate the quantity of non-specific copies to ensure that the DNA templates did not exceed an amount that would result in depletion of the PNA in the reaction based on comparisons to the threshold cycle of the MA DNA dilution series with known units of DNA.

The PNA/LNA PCR assay was subsequently optimized in melanoma cell lines. Fourteen melanoma cell lines were assessed for B-RAFmt (V600E), of which eight (57%) were found to have the B-RAFmt. The detection of B-RAFmt (V600E) was further validated by sequencing the genomic DNA of the cell lines.

B-RAFsmt in Melanoma Patients Sera.

Of 103 melanoma patients in the study, including patients treated with BC, 38 (37%) patients had B-RAFsmt detected in their serum. Furthermore, when the patients were divided based on early and advanced stages of disease, B-RAFsmt was detected in 11 of 34 (32%) early stage patients (AJCC Stage I/II), and in 27 of 69 (39%) with metastatic disease (AJCC Stage III/IV). B-RAFsmt was not detected in any of the 18 healthy normal donor serum samples.

B-RAFsmt in Stage IV Melanoma Patients.

The frequency of the B-RAFsmt in 50 stage IV melanoma patients prior to BC was compared to known prognostic factors in melanoma (Table 1). These factors included age, gender, ECOG status, the number of metastatic sites, the site of metastases (soft tissue, lymph nodes, and lung vs. other organs), lactate dehydrogenase (LDH) levels, and prior previous treatment (vaccine, chemotherapy, and/or interferon vs. no treatment). B-RAFsmt DNA was detected in 20 (42%) patients. The frequency of B-RAFmt and B-RAFwt DNA was compared to known prognostic factors. Of the factors considered, significant differences were seen in patients who had metastases in soft tissue, lymph nodes, and lung vs. other organs p<0.021), and patients who presented with higher LDH levels (p<0.027) (Table 1).

TABLE 1

Frequency of B-RAFsmt when compared to known clinical prognostic factors in stage IV melanoma patients receiving BC

| Clinical Factors | | B-RAFsmt (N = 20) | B-RAFwt (N = 30) | |
|---|---|---|---|---|
| Age | Mean ± SD | 43.4 ± 10.8 | 45.9 ± 11.8 | P = 0.629 |
| | ≤50 | 15 | 19 | P = 0.386 |
| | >50 | 5 | 11 | |
| Gender | F | 4 | 8 | P = 0.740 |
| | M | 16 | 22 | |
| ECOG | 0-1 | 8 | 18 | P = 0.166 |
| | 2 | 12 | 12 | |
| Met Sites | | | | |
| | 1-2 | 10 | 20 | P = 0.239 |
| | ≥3 | 10 | 10 | |
| ST/LN/ Lung only | | 2 | 12 | P = 0.021 |
| Other | | 18 | 18 | |
| CNS Met | | 15 | 28 | P = 0.100 |
| LDH | | | | |
| | Mean ± SD | 500.4 ± 857.2 | 295.2 ± 280.7 | P = 0.037 |
| | ≤190 | 5 | 17 | P = 0.027 |
| | >190 | 15 | 13 | |

ST, soft tissue; LN, lymph node.
B-RAFwt at V600E.

In order to determine the prognostic significance of B-RAFsmt in patients after treatment with BC, clinicopathologic variables were compared by a univariate analysis (Table 2). Age and gender were not significant predictors of response to treatment. However, ECOG status (p=0.049), the site of metastases p=0.019), and LDH levels p=0.041) significantly predicted treatment response. The presence of pre-BC B-RAFsmt was not a significant predictor of response to treatment.

TABLE 2

Univariate analysis of response of BC patients

| Clinical Factors | | CR, PR, SD (N = 26) | PD (N = 24) | (Chi-square Test) |
|---|---|---|---|---|
| Age | Mean ± SD | 46.8 ± 11.9 | 42.9 ± 10.6 | P = 0.341 |
| | ≤50 | 15 | 19 | P = 0.104 |
| | >50 | 11 | 5 | |
| Gender | F | 5 | 7 | P = 0.411 |
| | M | 21 | 17 | |
| ECOG | 0-1 | 17 | 9 | P = 0.049 |
| | 2 | 9 | 15 | |
| Met Sites | | | | |
| # of Met Sites | 1-2 | 17 | 13 | P = 0.419 |
| | ≥3 | 9 | 11 | |
| ST/LN/ Lung only | | 11 | 3 | P = 0.019 |
| Other | | 15 | 21 | |
| LDH | Mean ± SD | 264.0 ± 259.0 | 500.0 ± 790.7 | P = 0.041 |
| | ≤190 | 14 | 8 | P = 0.144 |
| | >190 | 12 | 16 | |

Variables found to affect response to BC (p<0.05) upon univariate analysis were analyzed by Cox multivariate regression analysis. These variables included age, gender, ECOG status, number of metastatic sites, site of metastases (soft tissue, lymph nodes, and lung vs. other organs), lactate dehydrogenase (LDH) levels, and prior previous treatment (vaccine, chemotherapy, and/or interferon vs. no treatment). Of the factors considered, only ECOG status (HR 0.24, 95% CI: 0.06, 0.98, p=0.047), site of metastases (HR 11.5, 95% CI: 1.62-82.5, p=0.015), and previous treatment (chemotherapy and/or interferon vs. no treatment; HR 0.12, 95% CI: 0.02, 0.92, p=0.041) were significant predictors of tumor response to BC. However, the presence of pre-BC B-RAFsmt (HR 2.2, 95% CI: 0.49, 9.80, p=0.30) did not significantly correlate with tumor response to BC.

Circulating B-RAFsmt and Survival.

Figure 2:
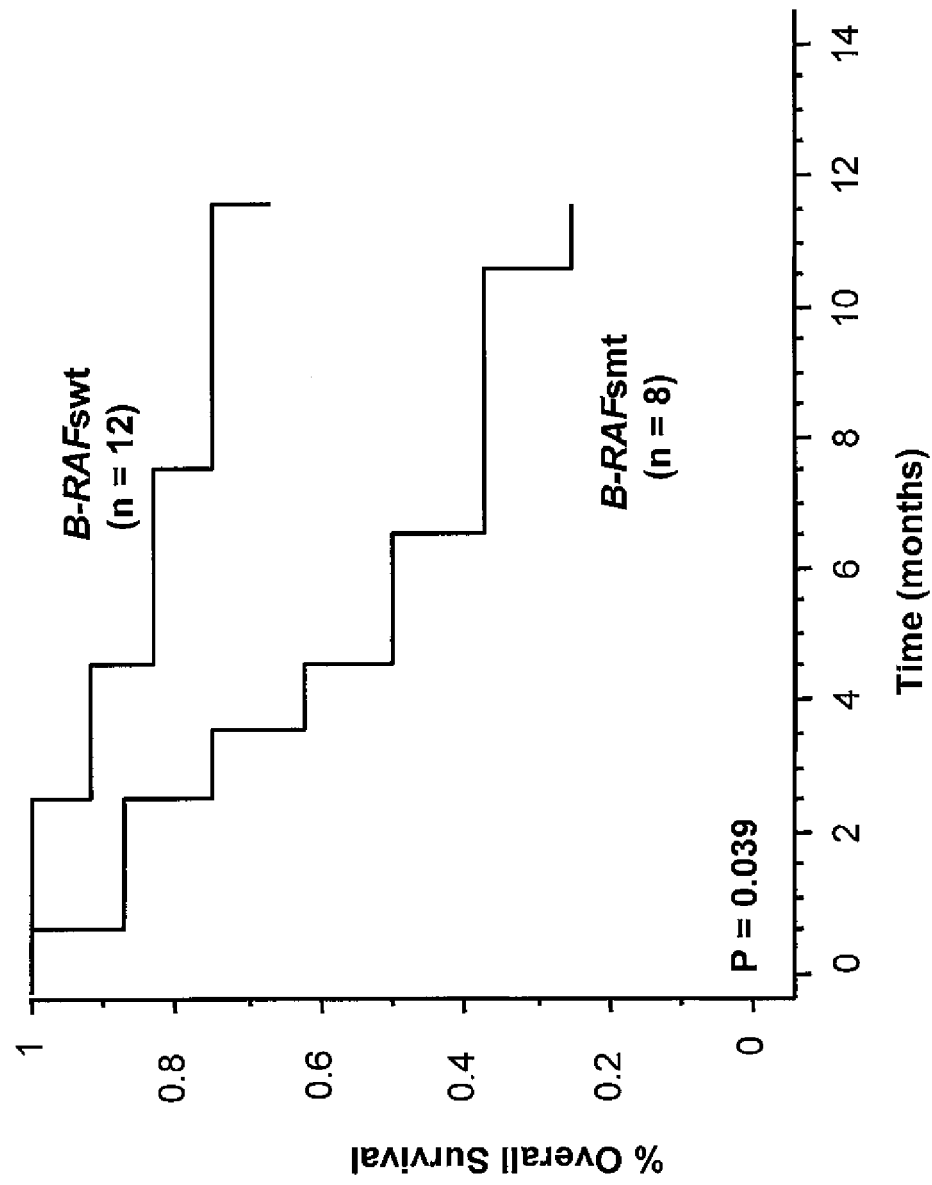
FIG. 2 shows Kaplan-Meier survival curves of BC patients. Correlation of post-BC serum B-RAF status, B-RAFsmt and B-RAFswt, with overall survival (log rank test, P=0.039).

Kaplan-Meier curves were developed to determine whether the B-RAFsmt correlated with overall survival (FIG. 2). A significant difference in overall survival was present between the 20 patients with the B-RAFsmt prior to BC compared to those that did not have the B-RAFsmt (median 13 vs. 30.6 mos, respectively; log-rank, p=0.039).

B-RAFsmt in Response to BC.

Figure 3:
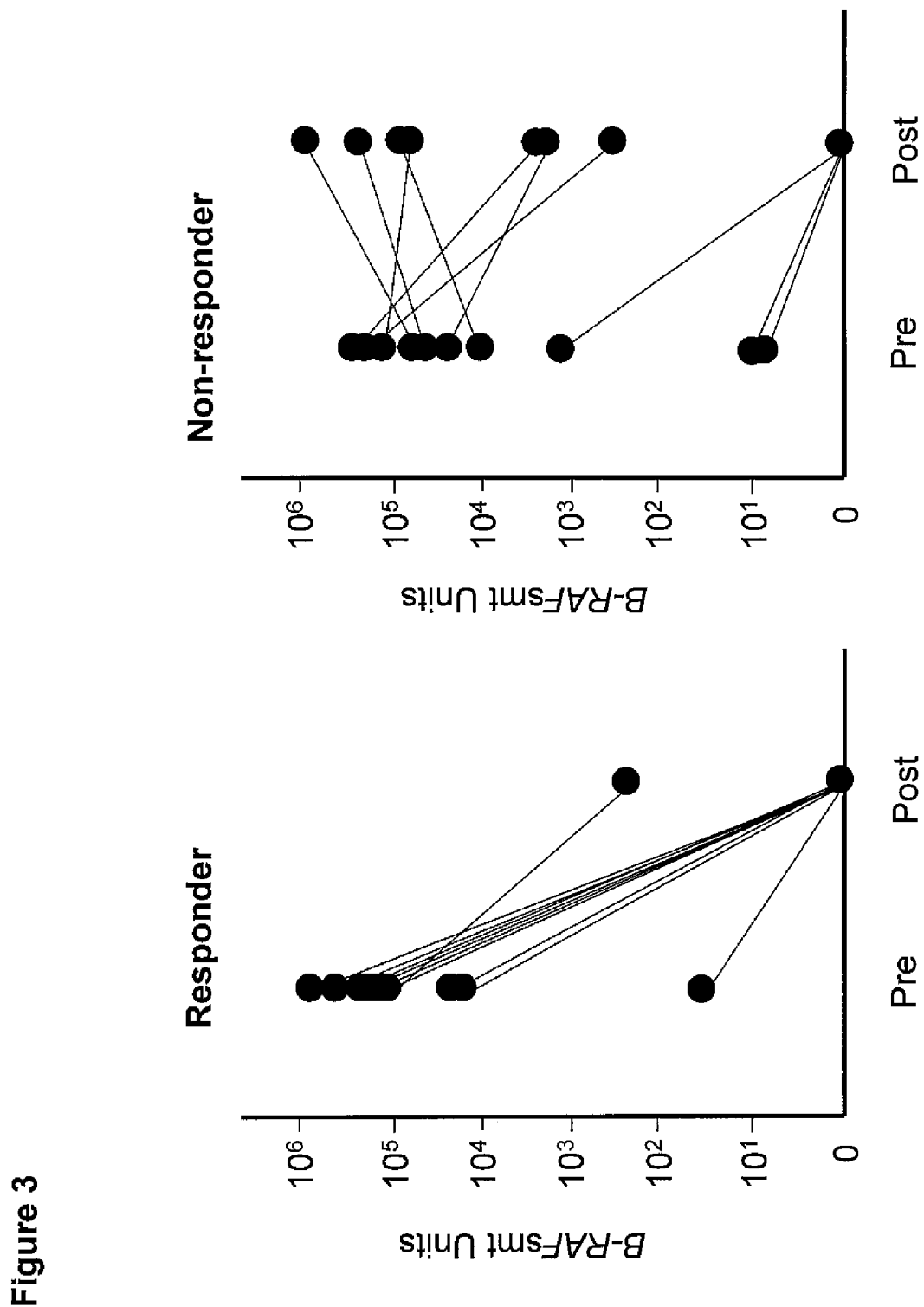
FIG. 3 illustrates DNA concentration of circulating B-RAFsmt in serum of responders and non-responders after BC treatment.

In assessing the change in the detection of circulating B-RAFsmt in response to BC (N=48), serum from ten of 24 (42%) patients were detected positive for the presence of the B-RAFsmt in the responder group and ten of 24 (42%) in the non-responder group (FIG. 3). However, post-BC treatment, circulating B-RAFsmt was detected in only one of the ten (10%) patients found to have circulating B-RAFsmt in their pre-BC treatment serum in the responder group. In contrast, for the non-responder group, a statistically significant number of patients (7 of 10, 70%; p=0.02) continued to have circulating B-RAFsmt in their post-BC treatment serum (Table 3). In 30 of the patients, we were able to assess respective melanoma tissues (primary, metastasis). Ten of these patients were pre-BC B-RAFsmt positive and had 100% concordance in having B-RAFmt (V600E).

TABLE 3

B-RAFsmt status in response to BC

| | Response | Non-response |
|---|---|---|
| Pre B-RAFsmt/Post B-RAFsmt | 1 (10%) | 7 (70%) |
| Pre B-RAFsmt/Post B-RAFswt | 9 (90%) | 3 (30%) |
| Total | 10 (100%) | 10 (100%) |

Comparison of response to non-response P = 0.02

In the single patient for the responder group with circulating B-RAFsmt found in post-treatment serum DNA, we observed that the ratio of the B-RAFsmt copy number to total serum B-RAFwt in serum (B-RAFswt) copy number was drastically reduced from that of the pre-BC treatment serum sample; 0.11 (pre-treatment) to 0.0021 (post-treatment). However, the three patients in the non-responder group whose post-BC treatment serum showed absence of circulating B-RAFsmt had low mutant to B-RAFswt ratios in their pre-BC treatment serum. The pre-treatment B-RAFsmt to B-RAFswt DNA ratio in serum ranged from $1.5 \times 10^{-3}$ to $9.0 \times 10^{-6}$ in these three patients, whereas the ratio was substantially higher in the other pre-BC treatment serum samples.

In comparing the pre-BC treatment sera to the post-BC treatment sera, we observed that the B-RAFsmt DNA ratio decreased in all 24 patients in the responder group and 20 of 24 patients in the non-responder group. Of the remaining patients in the non-responder group, one patient was found to have increased, and three had 'no remarkable changes' in the B-RAFsmt DNA ratio. This observation may have been related to the possibility that circulating B-RAFsmt was not detected due to insufficient amounts of DNA.

Discussion

The frequency of B-RAFmt (V600E and other sites) in patients with metastatic melanoma has been reported to be >55% (28-31). B-RAFmt has been suggested to contribute to the development of melanoma; however, this topic has been under debate. Primary melanomas of different types vary in B-RAFmt frequency. In the BC group studied, 43 of the 50 patient (93%) primaries identified were of cutaneous origin. The importance of mutations in both the N-RAS and B-RAF genes in dysplastic nevi and melanomas has been of considerable interest in that deregulation of the RAS-RAF-MEK-ERK pathway may be important in melanoma progression (2, 14). Since the B-RAFmt (V600E) has been shown to occur frequently in metastatic melanoma, it is important to determine if B-RAFmt V600E can be used to detect patients with metastatic melanoma and identify which patients would potentially be more responsive to specific adjuvant therapies.

In this study, we used a highly specific assay that recognizes a single base-pair mismatch to detect the B-RAF mutation at V600E. This is the first study demonstrating ability to detect B-RAFsmt in melanoma patients and potential clinical utility of predicting response to BC. In stage 1V patients who underwent BC, a significant number of patients p=0.02) who did not respond to BC continued to have circulating B-RAFsmt after the completion of treatment. Moreover, only one patient with a clinical response to BC was found to have circulating B-RAFsmt. The presence of B-RAFsmt in these patients indicated a lack of clinical response. The explanation for the lack of B-RAFsmt in responding patients is that tumors responding to BC undergo apoptosis, thus inducing DNA to break down into small fragments, which, when shed into body fluids, get rapidly cleared away. In non-responding patients, DNA can be released by tumor cell turnover, physical disruption of circulating tumor cells, and/or from tumor necrosis. The DNA released from these processes may not have gone through apoptosis processes, thus maintaining the DNA integrity and released as longer sized fragments.

Although presence of the B-RAFsmt did not significantly correlate with treatment response when compared to other known prognostic factors such as location of metastases, LDH levels, and prior treatment, the presence of post-BC circulating B-RAFsmt in patients did correlate with significantly poorer outcomes, such as decreased overall survival.

This pilot study demonstrates the potential clinical utility of monitoring patients with metastatic melanoma receiving therapy. Since studies have shown the frequency of B-RAFmt (V600E) in metastatic melanoma tissue to be higher than primary tumors, the serum assay may also be useful in patient follow up for monitoring disease progression (13, 32-34). There are reports suggesting that B-RAFmt (V600E) may be important in disease progression and may potentially be of prognostic utility (29, 32, 34). Our current findings showed no significant correlation with known clinical parameters that have been shown to affect outcome.

In conclusion, our findings confirm that the presence of the B-RAFsmt in circulating DNA in serum may have clinical utility in predicting tumor response and disease outcome. Although B-RAFsmt was not associated with other markers of disease progression, our study did show that the presence of the mutation confers poor outcomes with significantly lower overall survival. The raf-kinase inhibitor sorafenib (BAY 43-9006), which inhibits melanoma and other cancers by targeting the RAF/MEK/ERK pathway (3, 35, 36), has been FDA approved for renal cell carcinoma. BAY 43-9006 used alone has been disappointing in melanoma patients. The combination of BAY 43-9006 with other drugs may have benefits to melanoma patients. The detection of circulating B-RAFsmt prior to initiation of therapy may be very useful in monitoring treatment response to RAF/MEK/ERK pathway targeted drugs.

REFERENCES

1. Martinez S R, Takeuchi H, Hoon D S. Clinical Utility of RNA and DNA Molecular Markers as Prognostic Indicators of Disease Outcome and Response to Therapy in Malignant Melanoma. In: V J Hearing and S P Leong (eds.), Melanocytes to Melanoma: The Progression to Malignancy. Totowa, N.J.: Humana Press, 2006.
2. Gray-Schopfer V C, da Rocha Dias S, Marais R. The role of B-RAF in melanoma. Cancer Metastasis Rev 2005; 24: 165-183.
3. Wilhelm S M, Carter C, Tang L, et al. BAY 43-9006 exhibits broad spectrum oral antitumor activity and targets the RAF/MEK/ERK pathway and receptor tyrosine kinases involved in tumor progression and angiogenesis. Cancer Res 2004; 64: 7099-7109.
4. Robinson M J, Cobb M H. Mitogen-activated protein kinase pathways. Curr Opin Cell Biol 1997; 9: 180-186.
5. Kim J, Giuliano A E, Turner R R. Lymphatic mapping establishes the role of BRAF mutation in papillary thyroid cancer. Ann Surg 2006; In Press.
6. Naoki K, Chen T H, Richards W G, Sugarbaker D J, Meyerson M. Missense mutations of the BRAF gene in human lung adenocarcinoma. Cancer Res 2002; 62: 7001-7003.

7. Cohen Y, Xing M, Mambo E, et al. BRAF mutation in papillary thyroid carcinoma. J Natl Cancer Inst 2003; 95: 625-627.
8. Davies H, Bignell G R, Cox C, et al. Mutations of the BRAF gene in human cancer. Nature 2002; 417: 949-954.
9. Mercer K E, Pritchard C A. Raf proteins and cancer: B-Raf is identified as a mutational target. Biochim Biophys Acta 2003; 1653: 25-40.
10. Wan P T, Garnett M J, Roe S M, et al. Mechanism of activation of the RAF-ERK signaling pathway by oncogenic mutations of B-RAF. Cell 2004; 116: 855-867.
11. Kolch W. Meaningful relationships: the regulation of the Ras/Raf/MEK/ERK pathway by protein interactions. Biochem J 2000; 351 Pt 2: 289-305.
12. Weber A, Hengge U R, Urbanik D, et al. Absence of mutations of the BRAF gene and constitutive activation of extracellular-regulated kinase in malignant melanomas of the uvea. Lab Invest 2003; 83: 1771-1776.
13. Shinozaki M, Fujimoto A, Morton D L, Hoon D S. Incidence of BRAF oncogene mutation and clinical relevance for primary cutaneous melanomas. Clin Cancer Res 2004; 10: 1753-1757.
14. Smalley K S. A pivotal role for ERK in the oncogenic behaviour of malignant melanoma? Int J Cancer 2003; 104: 527-532.
15. Satyamoorthy K, Li G, Gerrero M R, et al. Constitutive mitogen-activated protein kinase activation in melanoma is mediated by both BRAF mutations and autocrine growth factor stimulation. Cancer Res 2003; 63: 756-759.
16. Mori T, O'Day S J, Umetani N, et al. Predictive utility of circulating methylated DNA in serum of melanoma patients receiving biochemotherapy. J Clin Oncol 2005; 23: 9351-9358.
17. Taback B, O'Day S J, Boasberg P D, et al. Circulating DNA microsatellites: molecular determinants of response to biochemotherapy in patients with metastatic melanoma. J Natl Cancer Inst 2004; 96: 152-156.
18. Hoon D S, Spugnardi M, Kuo C, Huang S K, Morton D L, Taback B. Profiling epigenetic inactivation of tumor suppressor genes in tumors and plasma from cutaneous melanoma patients. Oncogene 2004; 23: 4014-4022.
19. Mori T, O'Day S J, Martinez S R, et al. Estrogen receptor-alpha methylation predicts melanoma progression. Cancer Res 2006; In Press.
20. Paulasova P, Pellestor F. The peptide nucleic acids (PNAs): a new generation of probes for genetic and cytogenetic analyses. Ann Genet 2004; 47: 349-358.
21. Taback B, Bilchik A J, Saha S, et al. Peptide nucleic acid clamp PCR: a novel K-ras mutation detection assay for colorectal cancer micrometastases in lymph nodes. Int J Cancer 2004; 111: 409-414.
22. O'Day S J, Gammon G, Boasberg P D, et al. Advantages of concurrent biochemotherapy modified by decrescendo interleukin-2, granulocyte colony-stimulating factor, and tamoxifen for patients with metastatic melanoma. J Clin Oncol 1999; 17: 2752-2761.
23. O'Day S J, Boasberg P D, Piro L, et al. Maintenance biotherapy for metastatic melanoma with interleukin-2 and granulocyte macrophage-colony stimulating factor improves survival for patients responding to induction concurrent biochemotherapy. Clin Cancer Res 2002; 8: 2775-2781.
24. Sarantou T, Chi D D, Garrison D A, et al. Melanoma-associated antigens as messenger RNA detection markers for melanoma. Cancer Res 1997; 57: 1371-1376.
25. Bostick P J, Chatterjee S, Chi D D, et al. Limitations of specific reverse-transcriptase polymerase chain reaction markers in the detection of metastases in the lymph nodes and blood of breast cancer patients. J Clin Oncol 1998; 16: 2632-2640.
26. Hoon D S, Wang Y, Dale P S, et al. Detection of occult melanoma cells in blood with a multiple-marker polymerase chain reaction assay. J Clin Oncol 1995; 13: 2109-2116.
27. Fujiwara Y, Chi D D, Wang H, et al. Plasma DNA microsatellites as tumor-specific markers and indicators of tumor progression in melanoma patients. Cancer Res 1999; 59: 1567-1571.
28. Maldonado J L, Fridlyand J, Patel H, et al. Determinants of BRAF mutations in primary melanomas. J Natl Cancer Inst 2003; 95: 1878-1890.
29. Dong J, Phelps R G, Qiao R, et al. BRAF oncogenic mutations correlate with progression rather than initiation of human melanoma. Cancer Res 2003; 63: 3883-3885.
30. Chang D Z, Panageas K S, Osman I, Polsky D, Busam K, Chapman P B. Clinical significance of BRAF mutations in metastatic melanoma. J Transl Med 2004; 2: 46.
31. Chudnovsky Y, Khavari P A, Adams A E. Melanoma genetics and the development of rational therapeutics. J Clin Invest 2005; 115: 813-824.
32. Omholt K, Platz A, Kanter L, Ringborg U, Hansson J. NRAS and BRAF mutations arise early during melanoma pathogenesis and are preserved throughout tumor progression. Clin Cancer Res 2003; 9: 6483-6488.
33. Akslen L A, Angelini S, Straume O, et al. BRAF and NRAS mutations are frequent in nodular melanoma but are not associated with tumor cell proliferation or patient survival. J Invest Dermatol 2005; 125: 312-317.
34. Houben R, Becker J C, Kappel A, et al. Constitutive activation of the Ras-Raf signaling pathway in metastatic melanoma is associated with poor prognosis. J Carcinog 2004; 3: 6.
35. Flaherty K T. Chemotherapy and targeted therapy combinations in advanced melanoma. Clin Cancer Res 2006; 12: 2366s-2370s.
36. Stadler W M. Targeted agents for the treatment of advanced renal cell carcinoma. Cancer 2005; 104: 2323-2333.

The contents of all publications cited herein are incorporated by reference in their entirety.

What is claimed is:

1. A method of detecting a wild-type or mutant B-RAF gene in a subject, comprising:
    obtaining from a subject a body fluid sample containing DNA; and
    detecting a wild-type or mutant B-RAF gene in the sample by hybridizing the wild-type B-RAF gene to a peptide nucleic acid clamp and by hybridizing the mutant B-RAF gene to a locked nucleic acid probe,
wherein the mutant B-RAF gene contains a B-RAF V600E mutation.

2. The method of claim 1, wherein the body fluid sample is a blood, plasma, serum, or cerebral spinal fluid sample.

3. The method of claim 1, further comprising, prior to the step of detecting, combining in a vessel the body fluid sample, the peptide nucleic acid clamp, and the locked nucleic acid probe.

4. A method of treating cancer in a subject, comprising:
    obtaining from a subject a body fluid sample containing DNA;
    detecting whether a mutant B-RAF gene is present in the sample by hybridizing the wild-type B-RAF gene to a peptide nucleic acid clamp and by hybridizing the mutant B-RAF gene to a locked nucleic acid probe;

determining that the subject is likely suffering from cancer when the mutant B-RAF gene is present in the sample; and administering a cancer therapy to the subject likely suffering from cancer, wherein the mutant B-RAF gene contains a B-RAF V600E mutation.

5. The method of claim 4, wherein the body fluid sample is a blood, plasma, serum, or cerebral spinal fluid sample.

6. The method of claim 4, wherein the cancer is melanoma, thyroid cancer, colorectal cancer, lung cancer, or neurocancer.

7. A method of treating cancer based on a predicted outcome, comprising:

obtaining a body fluid sample containing DNA from a test subject suffering from cancer;

detecting whether a mutant B-RAF gene is present in the sample by hybridizing the wild-type B-RAF gene to a peptide nucleic acid clamp and by hybridizing the mutant B-RAF gene to a locked nucleic acid probe;

predicting, when the mutant B-RAF gene is present in the sample, that the test subject has a lower probability to survive or to be a responder to cancer therapy than a subject who suffers from cancer but does not have the mutant B-RAF gene; and administering a cancer therapy to the subject who suffers from cancer but does not have the mutant B-RAF gene, wherein the mutant B-RAF gene contains a B-RAF V600E mutation.

8. The method of claim 7, wherein the tissue sample is a paraffin-embedded tissue sample, and the body fluid sample is a blood, plasma, serum, or cerebral spinal fluid sample.

9. The method of claim 7, wherein the cancer is melanoma, thyroid cancer, colorectal cancer, lung cancer, or neurocancer.

10. The method of claim 7, wherein the cancer therapy is a biochemotherapy.

11. The method of claim 7, wherein the sample is obtained from the test subject prior to or following the therapy.

12. A method of monitoring the treatment of cancer, comprising:

obtaining (i) a first tissue or body fluid sample containing DNA from a subject suffering from cancer prior to treating the subject with a cancer therapy, and (ii) a second tissue or body fluid sample containing DNA from the subject after treating the subject with the cancer therapy;

detecting whether a mutant B-RAF gene is present in the first sample and the second sample by hybridizing the wild-type B-RAF gene to a peptide nucleic acid clamp and by hybridizing the mutant B-RAF gene to a locked nucleic acid probe;

determining that the subject is likely to respond to the therapy when the mutant B-RAF gene is present in a lower amount in the second sample as compared to the first sample; and administering additional cancer therapy to the subject that is likely to respond to the therapy, wherein the mutant B-RAF gene contains a B-RAF V600E mutation.

13. The method of claim 12, wherein the tissue sample is a paraffin-embedded tissue sample, and the body fluid sample is a blood, plasma, serum, or cerebral spinal fluid sample.

14. The method of claim 12, wherein the cancer is melanoma, thyroid cancer, colorectal cancer, lung cancer, or neurocancer.

15. The method of claim 12, wherein the cancer therapy is a biochemotherapy.

16. The method of claim 12, further comprising, after the step of detecting, continuing with the cancer therapy if the amount of B-RAF gene after the cancer therapy is less than the amount of the mutant B-RAF gene before the cancer therapy.

17. A method of treating cancer in a subject based on the status of the cancer, comprising:

obtaining a first body fluid sample containing DNA from a subject suffering from cancer at a first time point;

obtaining a second body fluid sample containing DNA from the subject at a second time point subsequent to the first time point;

detecting whether a mutant B-RAF gene is present in the first sample and the second sample by hybridizing the wild-type B-RAF gene to a peptide nucleic acid clamp and by hybridizing the mutant B-RAF gene to a locked nucleic acid probe;

determining (i) that the cancer has likely progressed in the subject when the mutant B-RAF gene is present in a higher amount in the second sample as compared to the first sample or (ii) that the cancer has likely regressed in the subject when the mutant B-RAF gene is present in a lower amount in the second sample as compared to the first sample; and administering a cancer therapy to the subject determined to have regressed cancer, wherein the mutant B-RAF gene contains a B-RAF V600E mutation.

18. The method of claim 17, further comprising, prior to the step of detecting, combining in a vessel the body fluid sample, the peptide nucleic acid clamp, and the locked nucleic acid probe.

* * * * *

UNITED STATES PATENT AND TRADEMARK OFFICE
CERTIFICATE OF CORRECTION

| | | |
|---|---|---|
| PATENT NO. | : 9,556,491 B2 | Page 1 of 1 |
| APPLICATION NO. | : 12/037798 | |
| DATED | : January 31, 2017 | |
| INVENTOR(S) | : Dave S. B. Hoon | |

It is certified that error appears in the above-identified patent and that said Letters Patent is hereby corrected as shown below:

In the Specification

At Column 1, Lines 13-16, delete "This invention was made with support in part by grants from NIH (POCA029605, POCA012582, and R33-CA100314). Therefore, the U.S. government has certain rights." and insert -- This invention was made with government support under CA029605, CA012582, and R33 CA100314 awarded by NIH. The government has certain rights in the invention. --, therefor.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*